US009974681B2

(12) United States Patent
Brown

(10) Patent No.: US 9,974,681 B2
(45) Date of Patent: May 22, 2018

(54) ORTHOPEDIC DEVICE FOR THE TREATMENT OF CAPSULITIS

(76) Inventor: Adam C. Brown, Hollywood, SC (US)

( * ) Notice: Subject to any disclaimer, the term of this patent is extended or adjusted under 35 U.S.C. 154(b) by 1058 days.

(21) Appl. No.: 12/786,933

(22) Filed: May 25, 2010

(65) Prior Publication Data
US 2011/0295171 A1    Dec. 1, 2011

(51) Int. Cl.
*A61F 5/00* (2006.01)
*A61F 5/01* (2006.01)

(52) U.S. Cl.
CPC .................................. *A61F 5/019* (2013.01)

(58) Field of Classification Search
CPC ...... A61F 5/019; A61F 13/068; A61F 13/063; A61F 13/06; A61F 13/064; A61F 2013/0048
USPC ......................................................... 602/30
See application file for complete search history.

(56) References Cited

U.S. PATENT DOCUMENTS

| | | | |
|---|---|---|---|
| 2,533,601 A | 12/1950 | McCormick | |
| 2,573,363 A | 10/1951 | Ruddick | |
| 2,591,378 A | 4/1952 | Scholl | |
| 2,633,129 A | 3/1953 | Crawford | |
| 2,646,795 A * | 7/1953 | Scholl | 128/894 |
| 2,711,166 A | 6/1955 | Digate | |
| 2,786,466 A | 3/1957 | Rudnick | |
| 2,797,686 A | 7/1957 | Crawford | |
| 2,797,687 A | 7/1957 | Crawford | |
| 2,835,248 A | 5/1958 | Scholl | |
| 2,835,379 A | 5/1958 | Scholl | |
| 2,847,004 A | 8/1958 | Lowth | |
| 2,917,846 A | 12/1959 | Scholl | |
| 3,253,591 A | 5/1966 | Scholl | |
| 5,497,789 A * | 3/1996 | Zook | 128/893 |
| 2008/0307678 A1 | 12/2008 | Nguyen et al. | |

* cited by examiner

*Primary Examiner* — Victoria J Hicks

(57) ABSTRACT

There are provided orthopedic devices suitable for the treatment of degenerative joint disease of the metatarsal phalangeal joints, in particular for the treatment of capsulitis. These orthopedic devices have a base portion designed to be placed under the foot only in the metatarsal area. A digit loop surrounding a toe is used to hold the base portion in the proper location. In one embodiment the digit loop is molded to or is an actual part of the base. The loop is preferably made of a gel material and provides cushioning in the toe because the gel dissipates the pressure. In another embodiment the digit loop is a detachable, adjustable loop. The device includes a raised cushioning pad of appropriate height and size affixed to the upper side of the base and resting against the foot when in use. The orthopedic device is preferably made entirely from a low-profile, viscoelastic gel.

5 Claims, 1 Drawing Sheet

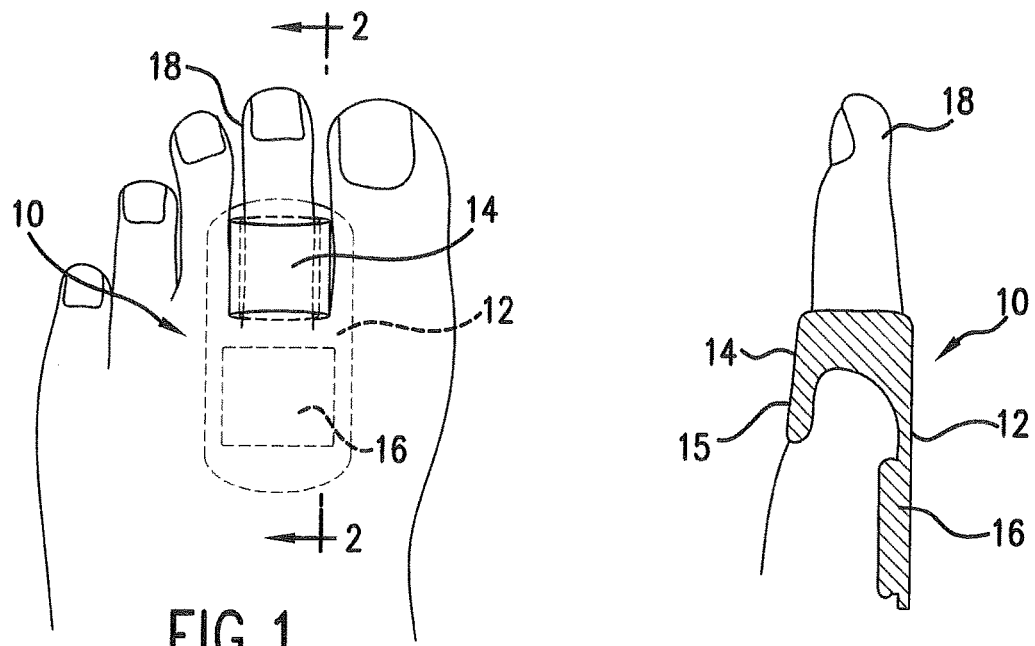
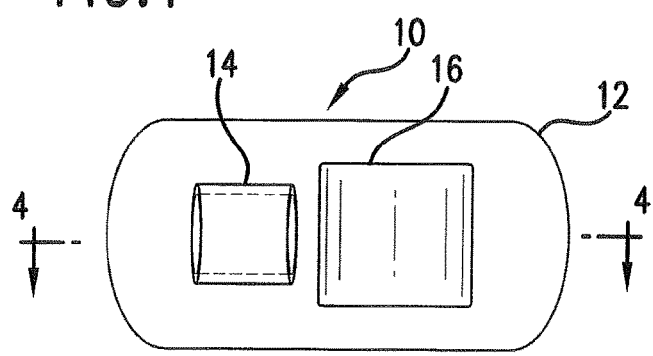
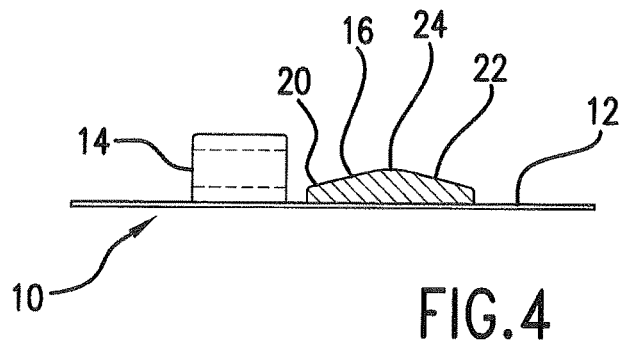

ORTHOPEDIC DEVICE FOR THE TREATMENT OF CAPSULITIS

BACKGROUND OF THE INVENTION

1. Field of the Invention

The present invention relates to an orthopedic device for the treatment of inflammatory conditions in the foot. More particularly, this invention relates to an orthopedic device for the treatment of degenerative joint disease of the metatarsal phalangeal joints, in particular a sub 2 splint for the treatment of capsulitis.

2. Description of Related Art

Capsulitis is an inflammatory condition that can occur at virtually any joint in the human body. In the foot, capsulitis is commonly found beneath the forefoot. Inflammation of the joint capsule of the forefoot is caused by excessive mechanical load being applied to the forefoot. The most common site where capsulitis occurs is beneath the second metatarsal head, but other sites can be affected. For example, when capsulitis involves the big toe joint; it is some times referred to as turf toe.

Prior treatment of forefoot capsulitis is generally found in ways to off load the forefoot. Among the treatments include rest, medications such as oral anti-inflammatories and cortisone injections, orthotics, different shoes and, as a last resort, surgery. Off loading is a technique that can be accomplished in many different ways, such as felt or foam latex metatarsal pads and the like. The difficulty with these types of pads is that proper placement may be a little tricky.

Many of the prior art devices for treating conditions of the foot are for treating corns, hammertoes, bunions and the like. The devices are primarily pads manufactured from compressible materials such as felt, latex and the like, and are retained in place using an adhesive. When such pads are not held in place using an adhesive, loops of a relatively narrow elastic or felt material are looped around the toe. This method of holding a foot pad in place has disadvantages such as causing friction against the toe and concentrations of pressure on the plantar digital arteries as it loops around the toe. Additionally, pads of foamed materials tend to lose their cushioning ability.

Despite prior efforts to produce a comfortable, effective orthopedic device for the treatment of degenerative joint disease of the metatarsal phalangeal joints, there remains a desire to produce an improved foot pad splint to treat degenerative joint disease of the metatarsal phalangeal joints and, in particular, immobilize the second digit and plantar structures of the second metatarsal phalangeal joints for treatment of sub 2 capsulitis.

SUMMARY OF THE INVENTION

It is therefore the general object of the present invention to provide an orthopedic device for the treatment of degenerative joint disease of the metatarsal phalangeal joints.

Another object of the present invention is to provide an orthotic sub 2 splint for the treatment of capsulitis.

Still another object of the present invention is to provide an orthopedic device having a digit loop with a dorsal end extending over the proximal phalange to position the device and provide immobilization of the plantar structures of the digit and the metatarsal phalangeal joint.

Yet another object of the present invention is to provide a foot cushion having a raised cushioning pad that is tapered from the center to the proximal end and the distal end.

An even further object of the present invention is to provide an orthopedic device for the treatment of plantar flexure, such as hammertoe.

The orthopedic devices of the present invention are especially suitable for the treatment of degenerative joint disease of the metatarsal phalangeal joints, in particular, for the treatment of capsulitis. These orthopedic devices comprise a base portion designed to be positioned under the foot in the area of inflammation. A digit loop surrounding a toe is affixed to or part of the base portion in such way as to hold the base portion in the proper position beneath the foot for maximum treatment and is preferably shaped to include a dorsal portion at the top to have an increased effect on the plantar flexion of the digit. In one embodiment the digit loop is molded to or is an actual part of the base portion. The loop is preferably made of a gel material and provides cushioning in the toe to dissipate the pressure. The orthopedic device includes a raised cushioning pad of appropriate height and size affixed to or part of the upper side of the base portion and resting against the foot when in use. The cushioning pad is higher in the middle and gradually tapers toward the proximal end and the distal end. The orthopedic device is preferably molded entirely of a low-profile, viscoelastic gel, molded as a single unit.

Other objects, features and advantages of the present invention will become apparent from the following detailed description of the invention taken in conjunction with the accompanying drawings.

BRIEF DESCRIPTION OF THE DRAWINGS

Having described the invention in general terms, reference will now be made to the accompanying drawings, which are not necessarily drawn to scale, and wherein:

FIG. 1 is a top view of a user's foot showing the orthopedic device of the present invention being positioned thereon with the base portion shown underneath the foot;

FIG. 2 is a side view of the orthopedic device of the present invention taken along line 2-2 of FIG. 1 showing a fixed splint digit loop having a dorsal portion immobilizing the second digit of a user's foot for treatment of sub 2 capsulitis;

FIG. 3 is a top view of the orthopedic device of the present invention shown in FIG. 2; and FIG. 4 is a side view of a different embodiment of the orthopedic device of the present invention showing the raised cushion having tapered ends taken along line 4-4 of FIG. 3.

DESCRIPTION OF THE PREFERRED EMBODIMENT(S)

The present invention now will be described more fully hereinafter with reference to the accompanying drawings, in which preferred embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art. Like numbers refer to the elements throughout.

The present invention relates to an orthopedic device for the treatment of inflammatory conditions in the foot. More particularly, this invention relates to an orthopedic device for the treatment of degenerative joint disease of the metatarsal phalangeal joints, in particular a sub 2 splint for the treatment of capsulitis. Referring now to FIG. 1 there is shown the orthopedic device 10 of the present invention in place on the foot of a user with the base portion 12 shown underneath the user's foot. In the embodiment shown in FIG. 1, when properly held in place against the bottom of the foot, the base portion 12 underlies the inflamed area. Although the orthopedic device 10 is preferably molded as a single piece, it may best be understood as having three components, such as shown in FIG. 3, namely, a base portion 12, a digit loop 14 surrounding a toe 18 and a raised cushioning portion 16.

The orthopedic device 10 comprises a base portion 12 designed to be positioned under the foot in the area of inflammation. Although the device is especially designed for treatment of the plantar structures of the second metatarsal phalangeal, it should be understood that the orthopedic device may be used to treat inflammation in other areas of the foot. The base portion 12 may vary in size, but when designed for treatment of the plantar structures of the second metatarsal phalangeal the base portion is generally from about 0.75 inches to about 1.5 inches wide, and from about 3.5 inches to about 5.0 inches long. The thickness of the base portion 12 should be as thin as practical and should not have a direct effect on the function of the splint. The base portion 12 is preferably made from a viscoelastic gel such as an organosiloxane.

A digit loop 14 surrounding the toe 18 is used to hold the base portion 12 in the proper location under the foot for maximum treatment, and is preferably shaped to include a dorsal portion 15 at the top to have an increased effect on the plantar flexion of the digit. As shown in FIG. 2, the dorsal portion extends proximally over the base of the digit. In another embodiment, that shown in FIG. 3, the digit loop 14 is about ¾" to 1 inch wide and is designed to surround the area between the proximal interphalangeal joint and metatarsal phalangeal joint. In another embodiment the digit loop is a detachable, adjustable loop. The digit loop 14 is preferably made of a gel material, such as a viscoelastic material, and is molded to or is an actual part of the base portion. It should be understood that the digit loop 14, as well as the other components of the orthopedic device, may be made of other materials such as felt, elastic or the like.

The orthopedic device 10 includes a raised cushioning portion 16 under the metatarsal head and metatarsal phalangeal joint. As shown in FIG. 3, the raised cushioning portion 16 is of appropriate height and size and part of or affixed to the upper side of the base portion 12 and resting against the foot when in use. The raised cushioning portion 16 is preferably made of a low-profile, viscoelastic gel. The raised cushioning portion 16 is generally from ¹⁄₁₆" to ³⁄₁₆" in height. In a preferred embodiment, that shown in FIG. 4, the raised cushioning portion 16 is tapered, i.e., lower at the distal end 20 and the proximal end 22 and slightly higher at the center 24. In this embodiment, the center is about ⅙ inch to ¼ A inch.

When in use, a toe 18 is placed through digit loop 14 of the orthopedic device 10 with the base portion 12 under the foot in the area of inflammation. As force is exerted downward on the raised cushioning portion 16 the gel begins to flow radially outward in a manner which increases the surface of contact between the gel and the foot. This increased surface area dissipates the weight over a larger area, resulting in a lower pressure per unit area. This force, tending to spread out the gel, is opposed by the intrinsic elastic properties of the viscoelastic gel. There will be no discrete pressure points found with the gel due to the unequal pressure applied by the irregularly-shaped foot. In those areas where pressure would build up in the conventional pad, the gel will flow radially outward and dissipate this pressure throughout the system in a "hydraulic" manner which is far superior to the way that pressure is dissipated in a non-compressible material.

Many modifications and other embodiments of the inventions set forth herein will come to mind to one skilled in the art to which these inventions pertain, having the benefit of the teachings presented in the foregoing descriptions. Therefore, it is to be understood that the inventions are not to be limited to the specific embodiments disclosed, and that modifications and other embodiments are intended to be included within the scope of the appended claims. Although specific terms are employed herein, they are used in a generic and descriptive sense only, and not for purposes of limitation.

What is claimed is:

1. A unitary orthopedic device for the treatment of degenerative joint disease of metatarsal phalangeal joints of a wearer's foot comprising:
    a thin, elongated base portion shaped and sized to fit underneath and along the length of said metatarsal phalangeal joints beneath said wearer's foot;
    a digit loop affixed to a front end of said base portion in such way as to position the base portion underneath said wearer's foot, said digit loop fitting around the toe of said wearer; and
    a raised portion having a distal end and a proximal end affixed to said base portion, said base portion being of sufficient height as to provide treatment of degenerative joint disease of said metatarsal phalangeal joints of said wearer.

2. The orthopedic device according to claim 1 wherein said orthopedic device is made of a viscoelastic gel.

3. The orthopedic device according to claim 1 wherein said raised portion is higher at the center of said raised portion between said distal end and said proximal end.

4. The orthopedic device according to claim 1 wherein said digit loop has a dorsal portion adapted to extend from the wearer's toe toward the wearer's foot capable of having an increased effect on plantar flexion of the wearer's foot.

5. An orthopedic device made as a unitary structure of a viscoelastic gel for treatment of capsulitis of metatarsal phalangeal joints of a wearer's foot comprising:
    a thin, elongated base portion from 3.5 inches to 5.0 inches long adapted to fit under the metatarsal phalangeal joints beneath said wearer's foot;
    a digit loop molded to a front end of said base portion in such way as to be capable of positioning said base portion underneath said wearer's phalangeal joints, said digit loop fitting around a toe of said wearer; and
    a raised portion having a distal end and a proximal end affixed to said base portion and configured to face said wearer's metatarsal phalangeal joints and of sufficient height to provide treatment of degenerative joint disease of said metatarsal phalangeal joints of said wearer, said raised portion being higher in the middle of said raised portion than at said proximal end and said distal end.

* * * * *